United States Patent [19]

Hoots

[11] Patent Number: 5,171,450
[45] Date of Patent: Dec. 15, 1992

[54] MONITORING AND DOSAGE CONTROL OF TAGGED POLYMERS IN COOLING WATER SYSTEMS

[75] Inventor: John E. Hoots, St. Charles, Ill.

[73] Assignee: Nalco Chemical Company, Naperville, Ill.

[21] Appl. No.: 672,190

[22] Filed: Mar. 20, 1991

[51] Int. Cl.$^5$ ............................................. C02F 5/12
[52] U.S. Cl. ................... 210/701; 73/861.07; 210/698; 210/745; 422/3; 422/16; 422/62; 436/56
[58] Field of Search ............... 210/698, 701, 745, 765; 73/861.07, 61.2; 422/3, 62, 16, 17; 436/2, 56

[56] References Cited

U.S. PATENT DOCUMENTS

| | | | |
|---|---|---|---|
| 4,783,314 | 11/1988 | Hoots et al. | 210/745 |
| 4,891,324 | 1/1990 | Pease et al. | 436/520 |
| 4,966,711 | 10/1990 | Hoots et al. | 210/745 |
| 4,992,380 | 2/1991 | Moriarty et al. | 436/147 |

Primary Examiner—Peter Hruskoci
Attorney, Agent, or Firm—Kinzer, Plyer, Dorn, McEachran & Jambor

[57] ABSTRACT

Method of determining treating agent concentration added to a water recirculating system to enhance efficiency by inhibiting scaling or corrosion or settling of particulates; the treating agent bears an amine-containing fluorescent moiety tag covalently bonded thereto, allowing sample analysis for emissivity as a measure of concentration equatable to the performance of treating agent in the system; by simultaneously employing an inert fluorescent tracer equated to the original (ppm) dosage of treating agent, consumption of the treating agent may be determined by emissivity differences equated to the original dosage.

11 Claims, 3 Drawing Sheets

MONITORING AND DOSAGE CONTROL OF TAGGED POLYMERS IN COOLING WATER SYSTEMS

FIELD OF THE INVENTION

This invention relates to continuous on-stream monitoring of the concentration of a treating agent added to cooling water systems and in particular water cooling towers of the form disclosed in my earlier patent, U.S. Pat. No. 4,783,314. Controlling the polymer dosage within specified ranges assists in maintaining scale/corrosion inhibition and particulate dispersancy performance of the water treatment program.

BACKGROUND OF THE INVENTION

The treating agent is responsible for inhibiting scale formation and corrosion in the system equipment and also for inhibiting formation of deposits and for preventing settling of suspended solids (dispersancy) on the system equipment, in particular the heat exchanger. In this role, the agent is consumed.

The treating agent is added in a predetermined concentration ("standard") to the cooling water, a standard concentration determined initially as most probably adequate for preventing scaling, corrosion and deposits. There may be several treating agents combined in one dose but collectively or individually they enhance performance of the system equipment by forming protective films thereon (corrosion inhibitor) or by adsorption onto unwanted particles (e.g. $CaCO_3$ and other scaling salts) to prevent their agglomeration or further growth, thereby preventing scale deposits of the system equipment.

As disclosed in my earlier patent, by including a known amount of an inert tracer (ppm fluorescent tracer, e.g. 2-naphthalene sulfonic acid, "2-NSA") with the treating agent, it is possible to measure and control the concentration of the treatment added to the system by measuring the emissivity of a sample of water and comparing it to the standard solution of the tracer. This is a highly accurate analysis because the fluorescent tracer is chosen s that it will not be affected by reaction with the system equipment (adsorption or deposition) nor will it react with any of the treating agents or natural impurities in the water. The tracer moves through the system as a discrete, unchanged entity as a true indicator of treatment concentration and characteristics of the cooling water system. Its integrity in other words is a constant, chemically and physically inactive with the system, although when calibrating the emissivity instrumentation it may be necessary to compensate for minor amounts of fluorescence which may be present in the system water (background fluorescence) or the treating agent.

In operation of a cooling tower, several important phenomena are involved: evaporation, "blowdown" to discharge collected impurities and replacement of the blowdown volume by "makeup" water.

Operating conditions may change (more or less blowdown for example) and as a consequence there may be a corresponding change in concentration of the inert tracer (and treatment dosage), determined by emissivity measure, calling for a higher feed rate of treatment when blowdown rate increases (an increased amount of untreated makeup water added to the system) and a lower feed rate of treating agent when blowdown rate decreases.

The inert tracer also serves as a diagnostic tool. Cooling tower systems are so complex that there are examples when the operators are not aware of system operations which are outside of specifications.

There are actually times when the chemical feed system (valve, pump, etc.) may fail or when unaccounted sources of makeup water enter the system. Such anomalies can be critical because clearly they change the treating agent concentration within the system which will be shown by changes in emissivity value of the inert tracer in the system water. Thus, an inordinate increase or decrease in blowdown from the system (or makeup water added to the system) will show up as an unexpected emissivity value as the system is sampled. When previous samples demonstrated that the system was operating properly, then unexpected changes in emissivity reading can serve as an indication of incorrect operation of the system and the cause of that incorrect operation.

Thus, if the emissivity reading of the inert tracer in the sample remains steady at a value corresponding to 100 ppm treating agent, then the concentration of treating agent is in conformance with the expected standard. But in the example of a volumetric change determined by an emissivity reading that does not compare to the standard dosage (e.g. 10 ppm decrease in treating agent concentration as determined by the inert tracer), then there is out-of-specification or non-standard operation of the system which requires an audit to identify and correct the incorrect operation of the system.

The foregoing presents a brief summary of the disclosure in U.S. Pat. No. 4,783,314. The entirety of that disclosure is incorporated herein by reference as constituting a known publication. In essence, use of an inert tracer enables volumetric changes in a circulating body of water to be detected with precision, the circulating body of water being one contained by or within the system equipment and one to which a treating agent is added and a portion of which will be consumed as it serves the role of inhibiting impurities likely to cause scaling, corrosion or deposit formation, any one of which can impair the efficiency of the equipment, especially the heat exchanger in a water cooling tower.

SUMMARY OF THE INVENTION

In industrial water systems, maintaining proper product or treating agent ("product") feed levels is essential for optimal performance. The proper product feed level is ultimately comprised both of the total concentration of the treatment and the concentrations of individual active components comprising the treatment. Active components such as polymers are added to provide scale/deposit inhibition, particle dispersion and to enhance activity of corrosion inhibitors.

However, it has been very difficult to quantitatively monitor and provide feedback control of active component concentrations (especially polymers), and the main object of the present invention is to be able effectively to monitor and compensate for the losses of the active polymeric component(s) of the treating agent as a consequence of attrition due to protective film formation on equipment (corrosion resistance) or avoiding deposits by adsorbing onto solid impurities to prevent agglomeration or crystal growth of particulates which can deposit on the equipment. When preventing scale formation, the treating agent may be performing in the role of a particulate dispersant or that of a "threshold inhibitor," analyzed in considerable detail in the NACE paper entitled *Influence of Mechanistic Studies on the Development of New Cooling Water Programs,* Paper No. 175 by John E. Hoots et al., Apr. 17-21, 1989. The subject is very complex. It is sufficient for purposes of this disclosure simply to recognize that the phenomenon of scaling in cooling water (and corrosion as well) can be inhibited by selection of an appropriate polymer (or combination of polymers) as the treating agent.

The use of polymers ("product" at times herein) with a carbonyl backbone, containing chemically-bound fluorescent or light-absorbing units, allows the concentration monitoring control task to be completed in accordance with the present invention, even at very low polymer concentrations. The benefits of this invention are as follows:

(1) to achieve a continuous record of polymer concentration with respect to time and direct indication of whether polymer level is maintained within specified limits, (2) to allow feedback control of polymer level in order to maintain polymer concentration within specified limits, (3) to observe the response of an active treatment or product component (polymer) to changes in operating conditions of the system (e.g. effect of scaling or corrosive conditions on the polymer level), (4) to accomplish performance responsive control of polymer level (e.g. if polymer level decreased due to scaling conditions, the monitor/feedback control equipment adds more to treatment to maintain a constant polymer level), and (5) to determine total polymer demand of the system by using an inert chemical tracer (measure of total product concentration) and subtracting product concentration as indicated from tagged polymer level, where changes in total polymer demand provide an indication of whether active component losses are excessive.

Polymers tagged with chemically-bound ultraviolet/visible light absorbing chromophores and fluorescent units are employed. The fluorescent units are disclosed in the pending application of Dodd W. Fong and John F. Hoots the disclosure of which is incorporated herein by reference. These units can be incorporated into the polymer by the following methods:

A. transamidation of acrylic acid/acrylamide copolymers with aromatic or alkylaromatic amines;

B. transamidation of acrylic acid/acrylamide copolymers with alkyl-aromatic aminoacids;

C. chain-transfer reaction with alkylaromatic hydrocarbon during polymerization process;

D. copolymerization with fluorescent monomer.

Light-adsorbing chromophores can also be incorporated into the polymers by similar synthesis methods.

The polymers of concern are water soluble, derived from acrylic acid, that is, polyacrylic acid polymers or derivatives thereof, namely, (for example) polyacrylic acid, polyacrylamide, polymethacrylamide, polysulfomethyacrylamide, polyvinyl acetate, polymethacrylic acid and polyacrylonitrile being the most notable. The molecular weight is typically about 2,000-100,000.

Generically, the acrylics are characterized by the presence of the carbonyl type group

(Formula I)

where R is —OR' or —NH$_2$ and wherein R' is hydrogen or a salt or a substituent other than hydrogen meaning a single or multivalent group other than hydrogen covalently bonded to a carbon or an organic molecule.

The pendant polymer group derivatized by the transamidation reaction may be contained in a polymer unit or mer unit (a portion of the polymer containing two adjacent backbone carbons) having the structure of Formula II:

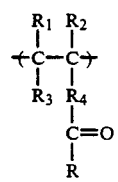

(Formula II)

wherein: $R_4$ is $C_nH_{2n}$, n is zero or an integer from 1 to about 10, $R_1$, $R_2$ and $R_3$ are independently hydrogen or a substituent other than hydrogen, and R is as defined above for Formula I, and salts thereof, and mixtures or combinations thereof.

The organic fluorescent derivatizing agent is an organic fluorescent molecule that contains an amine group, preferably a primary amine group. Such an agent may be represented by Formula III:

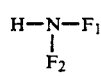

(Formula III)

wherein one of $F_1$ and $F_2$ may be, and preferably is, hydrogen and within at least one of $F_1$ and $F_2$ or within $F_1$ and $F_2$ together, is an organic fluorescent group. The transamidation derivatization reaction proceeds as follows:

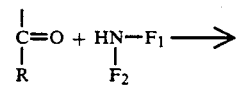

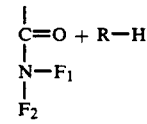

(Formula IV)

wherein the structure designated Formula IV above is a transamidation derivatized pendant group on the polymer. As seen from Formula IV, the derivatized pendant polymer group is a pendant N-substituted amide group having a fluorescent group within at least one of $F_1$ and $F_2$ or within $F_1$ and $F_2$ taken together. This reaction is an amidation reaction when R is —OR' and a transamidation reaction when R is —NH$_2$, and hence the term "transamidation" is used herein to specify either or both forms of the reaction. Thus, the fluorescent tag in the mer unit is a fluorescent moiety, preferably an amine-containing organic fluorescent moiety.

Since the treating agent by definition will undergo depletion in the circulating water system to prevent scaling, to prevent corrosion or to prevent deposits or precipitates, it becomes possible to observe expected performance. For example, past experience or analysis of the system water may reveal the polymer should be so fed that normal depletion of the polymer will be confirmed by an emissivity reading equivalent to (for example) 100 ppm. The emissivity value can be converted to a DC voltage analog as disclosed in pending (allowed) application Ser. No. 258,131, filed Oct. 14, 1988, now U.S. Pat. No. 4,992,380. This voltage analog is then transmitted to a pump controller having LO and HI set points corresponding to an acceptable range of (for example) 98–102 ppm treating agent; if the transmitted voltage value is less than LO, the controller increases the rate of the pump which feeds the treating agent; vice versa if the reading exceeds HI. Analog signals other than DC voltage (e.g. DC current or pulsed frequency) may also be used and analog signals may be interconverted (e.g. DC voltage converted to DC current).

DETAILED DESCRIPTION

Figure 1:
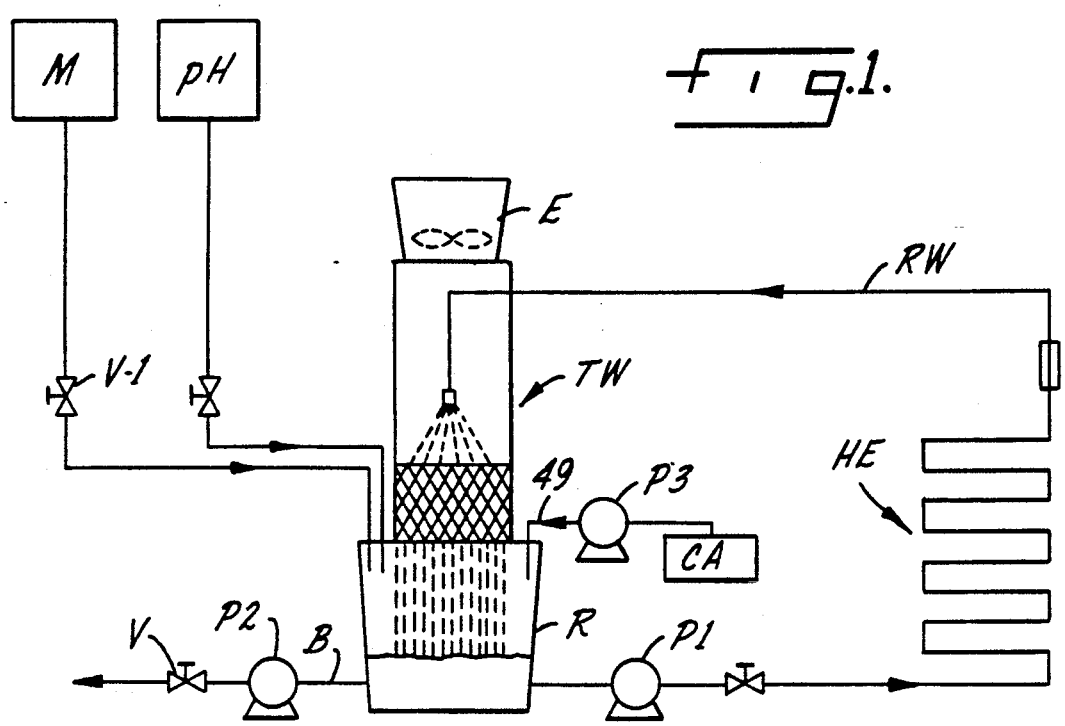
FIG. 1 is a schematic view of a cooling tower and related equipment.

FIG. 1 is a diagram of a typical water cooling tower system representative of a circulating water system in which the present invention may be employed.

The tower TW includes an evaporator E to which the recirculated water RW is fed, evaporative cooling of RW extracting heat from the system. The hot water is pumped from the tower reservoir or basin R by a pump P1 and sent to a heat exchanger HE where the water is heated. Blowdown B may take place from time to time when the concentration of impurities becomes too high, using pump P2 and (open) valve V. Valve V-1 is opened to introduce fresh makeup water.

The treating agent is fed to the tower water from a supply CA, using a controlled pump P3.

Figure 2:
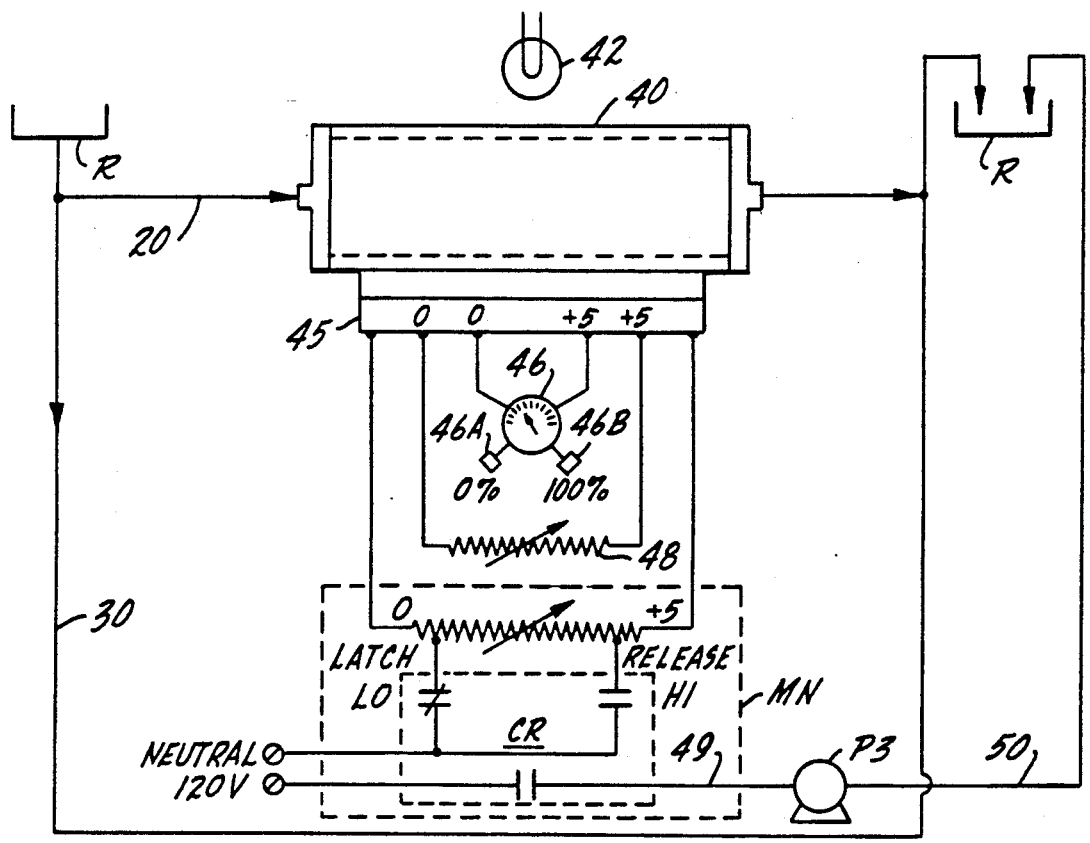
FIG. 2 is a schematic view of emissivity equipment and related instrumentation for generating and using a voltage analog of emissivity.

FIG. 2 shows how pump P3 is controlled. As will be described in more detail below, a sample 20 of the circulating cooling water is diverted from a bypass line 30 communicating with the reservoir R of the cooling tower. The sample is fed through a fluorometer flow cell where its emissivity (em) is measured and converted to a voltage analog as disclosed in said application Ser. No. 258,131. The emissivity can also be converted into a DC current or pulsed frequency signal. The term "analog signal" represents DC voltage, DC current or pulsed frequency signal and each signal type is interconvertible (voltage analog converted into current analog signal). The analog signal may also be used for continuous visual performance charting. A controller MN for pump P3 has the capability of determining if the analog signal is on either side of a pair of set points. The set points are HI (high) and LO (low) signifying that as long a the analog signal of the emissivity lies between the HI and LO set point values (parity), then there is no need for a change in the dosage of treating agents; but if there is disparity on either side then a HI signal or LO signal is transmitted to a transducer (not shown) for pump P3 which alters the pump rate accordingly to decrease or increase the rate of feeding the treating agent.

The instrumentation for continuous monitoring is presented in FIG. 2, schematically on an exaggerated scale, the same as in U.S. Pat. No. 4,992,380. A flow cell in the form of a quartz cylinder is identified by reference character 40. The flow cell is transparent to ultraviolet light emitted by a light source 42 directed against one side of the flow cell. At a 90° angle from the light source is a transducer 45 which transforms fluorescent emissivity into an analog signal (e.g. 0–5 volts DC), emissivity varying with fluorescent concentration.

A dial indicator 46 responds to the output (D.C.) voltage of the transducer 45 enabling the concentration of treating agent (ppm equivalent) to be observed. This dial has the two calibration knobs (46A, 46B) respectively set manually for 0% (no treatment) and 100% emissivity response of the analyzer.

A recorder for a hard printout of treating agent concentration is identified by reference character 48, responding on an analog signal (continuous line) basis to the transducer element included in the analyzer. The recorder is responsible for print-outs such as those shown in FIG. 4 et seq.

Finally, the monitor MN having HI, LO latching relay (CR) contacts is in communication with the output analog signal of the transducer which in effect evaluates the concentration of treating agent. If the evaluation does not compare favorably to the standard, the monitor transmits a control signal to control line 49 by which pump P3 is controlled, feeding the treating agent dosage to reservoir R (FIG. 2) through conduit 50. A typical field condition may call for 100 ppm treating agent. During 0% calibration knob 46A is used to set the dial pointer (46) to zero and knob 46B (100%) is used to set the dial pointer to read the equivalent of 200 ppm treating agent when calibrating with the standard solution of tagged treating agent.

There is invariably some background fluorescence in the cooling water. The amount of fluorescent tagging agent is sufficient to overcome this potential interference.

It is not practical, or even necessary, to operate the system precisely at the standard value, which, in this example, is 100 ppm (corresponding to a 50% setting of dial pointer 46). Thus, the dosage setpoints in the monitor (LO, HI) may be chosen as 98–102 ppm, and these values represent the standard for (parity) comparison, that is, the analog signal (0–5 volts DC in this case) of the measured on-stream emissivity is compared to the set points of the monitor. The corresponding LO, HI voltage range in the monitor MN may be 2.45 and 2.55 volts DC, which is to say that when the monitor detects a LO value of 2.45 volts DC a control signal is emitted to increase the pump rate which continues until the HI value of 2.55 volts DC is detected. In this connection, it is the treating agent concentration, under continuous flow, which is continuously monitored on a real-time basis, and not some unreliable and unselective operating parameter such as water gains or water losses, or grab sample averaging.

The standard for measuring performance initially is based on past knowledge of the factors of the system, including impurity concentrations, area of tubing to be protected against corrosion or scaling, volume of water and rate of water flow. Using such factors, it is possible to estimate the dosage of treating agent needed. If an operating factor (parameter) is in error, especially the estimated scaling tendency of the system which must be inhibited by the treating agent then non-standard performance may be due to a miscalculated dosage, and not due to unexpected changes in system volume or removal of treating agent (i.e., excessive blowdown, scaling, etc.). In any event, the treating agent dosage may be accurately trimmed to a prevailing cooling tower water system either by correcting the dosage when all operating parameters are accurately known, or by trouble shooting the system to identify unknown errors in the operating parameters. Non-standard performance may be due to large, unknown additions of makeup water, diluting the treating agent so that the dosage is not enough to inhibit particle agglomeration, scaling and/or corrosion. Non-standard performance may also be due to large, unknown blowdown losses, by which the dosage of treating agent is drastically lowered.

Figure 3:
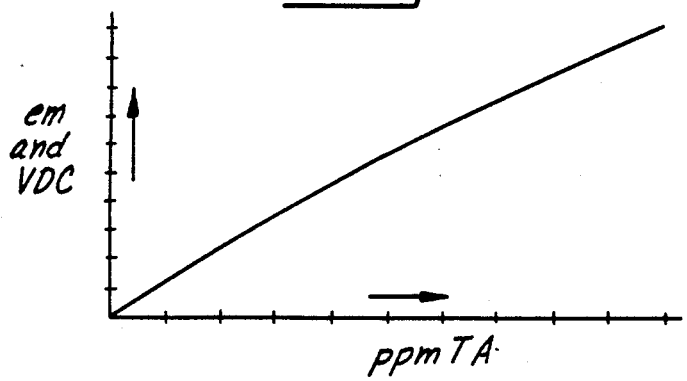
FIG. 3 is a graph of emissivity and its analog (VDC) vs. ppm.

While it will be readily apparent to those familiar with fluorescence and its equivalents in terms of an analog signal [e.g. DC voltage (VDC)] and emissivity (em), nonetheless FIG. 3 is included typically to show that emissivity and its voltage analog increase with ppm polymeric treating agent (TA) containing the fluorescent moiety on the carbonyl backbone of the circulating acrylic polymer.

Figure 4:
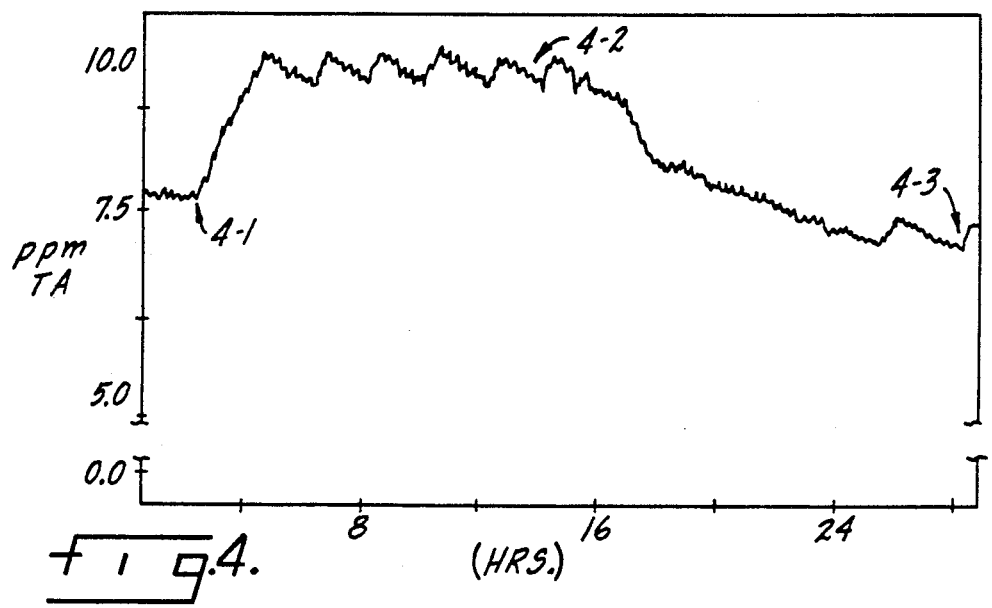
FIGS. 4, 5 and 6 are replica print-outs of real time monitoring of fluorescent tagged polymer.

Feasibility of continuously monitoring/controlling a fluorescently tagged polymer treatment in a cooling water program was demonstrated in a pilot cooling tower, FIG. 4. The polymer contained a fluorescent tag and was monitored/controlled with a commercial fluorometer unit of the type described in connection with FIG. 2. The polymer concentration control point was initially set at 7.5 ppm polymer actives (4-1, FIG. 4), then raised to 10 ppm (4-2), and finally lowered to 6.8 ppm (4-3).

Continuous monitoring of the tagged polymer also permitted troubleshooting, that is, an audit of system anomalies:
Makeup inlet valve failure, FIG. 5;
Chemical concentration changes due to makeup water addition, FIG. 6.

The sawtooth pattern (4 A.M. to 10 A.M., FIG. 5 for example) is typical for that system, due to on/off for the blowdown pump and makeup water inlet valves, evidencing the sensitivity of the present practice.

Figure 5:
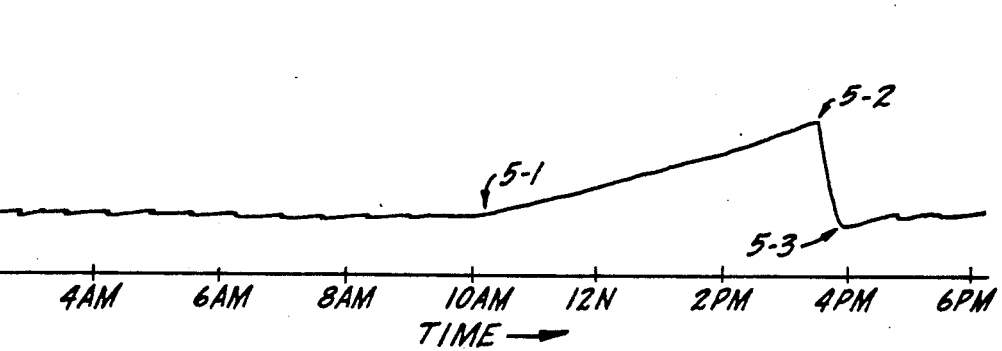

Midway through the test, FIG. 5, the makeup inlet valve V-1 stuck (at 5-1) in the closed position. This caused overcycling and greatly reduced system volume (blowdown pump on continuously). The point when the valve failed was clearly seen by monitoring the tagged polymer concentration. Thus, since the system volume decreased, the tagged polymer concentration increased, as shown by the rising slope 5-1 to 5-2, FIG. 5. When the makeup valve was restored to normal operation, (5-2), the system volume returned to a normal level, 5-3, FIG. 5.

Figure 6:
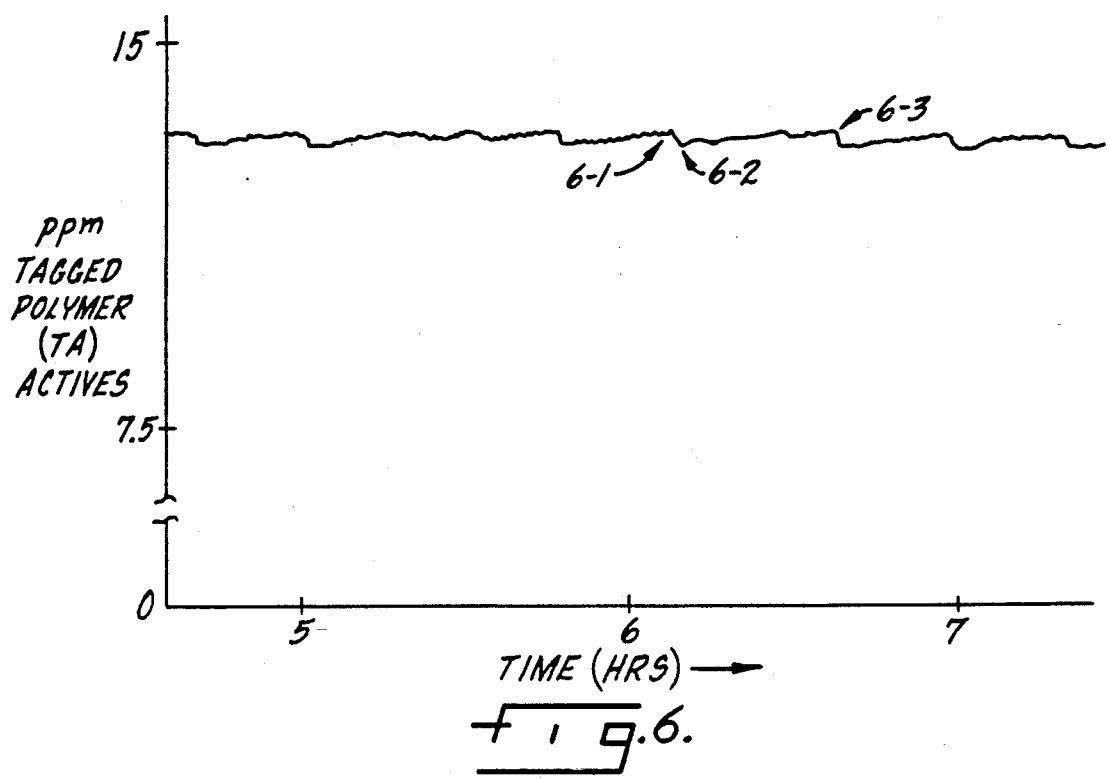

The rhythmic sawtooth pattern due to normal operation was repeatedly seen when monitoring the tagged polymer concentration, FIG. 6. The concentration changes are caused by makeup water being added, diluting the basin or reservoir volume by up to 3-4%, (6-1). With the makeup water valve turned off (6-2), the concentration of treatment or product slowly increases as evaporation of water occurs until the makeup water valve is opened, 6-3.

The ability to clearly observe and identify the source of polymer concentration changes is due to excellent stability and very low noise level ($\pm 0.05$ ppm polymer actives) in the fluorometer output signal.

The fluorescent tag was added via the transamidation process using acrylic acid/acrylamide polymer backbone and derivatizing it with 1-amino-7-naphthalenesulfonic acid and amino-methanesulfonic acid. The amine-containing derivatizing agents form N-substituted-acrylamide linkages with the polymer backbone.

Stated in other words, the test results (FIGS. 4–6) obtained in the pilot cooling tower demonstrated the following results:

1. ability to continuously monitor and control concentration of polymer containing fluorescent tag;

2. ability of fluorescent tag analysis to detect low levels of tagged polymer and control dosage to a very high level of accuracy;

3. ability to change target dosage for polymer concentration at will (FIG. 4, first target dosage at 7.5 ppm, next at 10 ppm, then back down to 6.8 ppm tagged polymer);

4. diagnosis of equipment failure (and return to normal operation) by monitoring tagged polymer concentration—refer to FIG. 5;

5. ability to visualize mechanical operation of cooling water system (FIG. 6, water being added to system, followed by subsequent evaporation of recirculating cooling water) by monitoring tagged polymer concentration.

Additional test results were obtained in a pilot cooling tower demonstrating the concept of monitoring two fluorescent sources in a cooling water system in which the purpose for using each was distinctly different. One source was an inert fluorescent tracer according to my earlier patent, e.g., 2-naphthalene sulfonic acid (2-NSA); the other source was the tagged polymer disclosed above.

Figure 7:
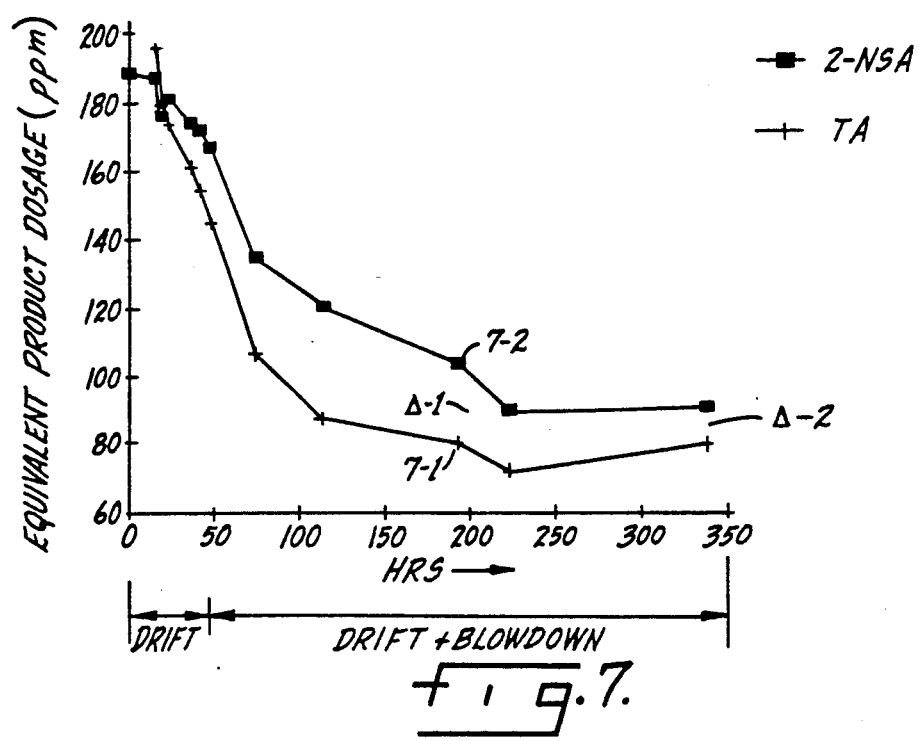
FIG. 7 is a replica print-out comparing equivalent ppm treating agent dosage (2× multiplier) as determined by inert fluorescent tracer (2-NSA) and fluorescent tagged polymer (demonstrating partial polymer depletion from scaling/corrosion processes).

The fluorescent tagged polymer serves to inhibit deposits, enhance activity of corrosion inhibitors, and disperse particulates in a water system. Since an active treatment component is likely to be incorporated into deposits (through adsorption processes), the fluorescence level of tagged polymer should be less than that of the inert fluorescent tracer (2-NSA), which indeed is the case as shown by FIG. 7. In this case, a 100 ppm dosage of treating agent contains 7.5 ppm (as actives) of the fluorescent tagged polymer and 0.40 ppm (as actives) of the inert fluorescent tracer. At 190 hours of elapsed time, the tagged polymer concentration was measured as 6.00 ppm actives (80 ppm equivalent treating agent dosage point 7-1) and the inert tracer concentration was measured as 0.42 ppm actives (105 ppm equivalent treating agent dosage point 7-2). At 105 ppm equivalent treating agent dosage, the expected concentration of tagged polymer is 7.88 ppm (as actives).

The difference between the expected (7.88 ppm actives) and observed (6.00 ppm actives) concentration of tagged polymer is due to incorporation of the tagged polymer into sites of scaling and corrosion. This difference is 1.88 ppm polymer actives denoted by the symbol delta-1 in FIG. 7. Thus, the difference in equivalent treating agent dosages (105 ppm expected, as determined by the inert tracer versus 80 ppm actual, as determined by the tagged polymer) is an equivalent measure of the loss of tagged polymer by incorporation into scaling and corrosion sites convertible by difference to ppm deposit (consumption) of the (tagged) polymer in its performance role. By measuring the loss of tagged polymer concentration (due to incorporation into scale and deposit sites) as indicated previously, it is possible to obtain a measure of treating agent performance. For example, if it is deemed that a loss of no more than 2.25 ppm actives of tagged polymer concentration (comparable to 30 ppm equivalent treating agent, that is, $30/100 \times 7.5$) will still provide acceptable inhibition of scaling corrosion and particulate dispersancy, then it is possible to adjust the operating conditions, dosage of treating agent, or composition of treating agent when needed so that performance criterion is met. In FIG. 7, the results indicate that performance of tagged polymer and treating agent as a whole are within the performance guidelines described above. After 340 hours, the difference (delta-2) is about 12 ppm, equating to about 0.9 ppm tagged polymer drop-out.

The foregoing explains the additional benefit of using a fluorescent tagged polymer as a gauge of product performance, continuously obtained by comparing fluorescence levels of inert vs. active fluorescent compounds. Again, the difference between those two fluorescence levels is typically caused by deposition/corrosion processes and adsorption onto existing particulates.

In FIG. 7, the sequence of events is as follows:

(1) 200 ppm of product is initially added at 0 hours.

(2) No blowdown of system water occurs until 50 hours of time has elapsed. Between 0-50 hours, the inert tracer level will decrease by a small amount due to drift (droplets of cooling water being ejected out of the system by cooling tower and fan). During the same time period, the tagged polymer level will decrease to a larger extent because of drift and adsorption of polymer onto the system surfaces and particulates.

(3) Once blowdown starts (at about 50 hours), the product is being fed at about 95-100 ppm dosage. It takes an additional 120-150 hours (170-200 hours total elapsed time) for the product dosage to decrease from 200 ppm (initial) to 95-100 ppm (maintenance) value.

The key observations regarding FIG. 7 are that:

(A) Concentration of inert tracer follows the expected behavior, based on pilot cooling tower operating conditions.

(B) Concentration of tagged polymer (as indicated by "equivalent product dosage") is lower than inert tracer, due to adsorption of the tagged polymer onto heat-exchange surfaces and particulates.

In further explanation of FIG. 7, the addition (ppm) of the tracer to the system is equivalent to the (ppm) concentration of the tagged polymer. This allows performance of the polymer to be determined. Once the system has equilibrated, arriving at a steady state (after about 200 hours) and assuming no volumetric anomalies (no unexpected water gains or losses) the concentration of the tracer (2-NSA) should remain fairly steady as the ppm equivalent of the polymer concentration construction (particularly evident after 225 hours). However, there may be evident "swings" at times of expected volumetric changes due to scheduled blowdown and/or makeup, with corresponding swings in ppm read-outs. The arithmetic difference or departure between the two ppm readings (whether the difference is positive or negative) allows a determination of treating agent consumption, whether on schedule (par performance), or too much or to little as an abnormality.

The ppm equivalent print-out line for the inert tracer is a track of volumetric changes due to water removal (blowdown) or addition (makeup) since the inert tracer undergoes neither chemical nor physical change throughout the entire water circulating system, unlike the polymer which is consumed (deposits out in one way or another) in its normal role. For par performance, in other words, the two print-out trace lines (FIG. 7) at equilibrium will be substantially parallel: the tracer (2-NSA) concentration equates to the original polymer dosage, and the polymer is being consumed (deposited out) at the expected rate. On the other hand, and again referring to FIG. 7, if the concentration of the tagged polymer TA should continue its divergence after 190 hours (without rising as shown) then this evidences the fact it is being consumed at an inordinate, unacceptable rate for some reason or another. Conversely, if ppm TA should elevate and cross the inert tracer line, this evidences that either too much treating agent is being used or the polymer product is not performing as it should. The dosage of treating agent is then altered accordingly in amount or kind.

The print-out coordinates (FIGS. 4 et seq.) present the best information. The horizontal time axis needs no explanation. The vertical axis denotes how concentration changes with time. Further as to FIG. 7, the vertical axis relates or indicates how much treating agent would have to be present to produce the observed levels of the tagged polymer analyte, assuring no accidental loss (or added source) of that analyte has occurred. It needs to be stressed that the dosage of polymer includes the actives (e.g. only 7.5 ppm tagged polymer) and the inactive tracer dissolved in the dosing diluent or carrier, usually water in which the actives are dissolved.

The vertical axis in FIG. 7, reads in terms of the dosage equivalent since the feed of product, of which the active (tagged) polymer is a small part, is the real matter of concern, to be controlled by varying the rate at which pump P3 doses the system.

The analyte fluorescent species (2-NSA and the amino naphthalene sulfonic acid tag) are chosen on the basis of sensitivity and lack of interference with performance of the polymer which is tagged, both clearly susceptible to substitution by equivalents.

As noted, the polymer identified with the data of FIGS. 4-7 had an acrylic acid/acrylamide backbone derivatized with 1-amino-7 napthalenesulfonic acid and amino-methane sulfonic acid, F1-F2. However, one site for fluorescence on the polymer backbone (F1 or F2) is sufficient and of course a host of water soluble polymers may be so tagged as equivalent practice within the purview of the specification and claimed subject matter. Not every mer unit in the polymer needs to be tagged; one to two weight percent of the total mer units is enough and this limited amount of tagging is capable of detection down to 1 ppb.

When highly fluorescent groups are employed, the fluorescent derivatizing agent may be used in amounts as low as about 0.5 mole percent of the polymer. Polymers have been provided with very high degrees of fluorescent detectability using about 1 mole percent fluorescent derivatizing agent. While the maximum amount of fluorescent groups that may be incorporated into the polymer is limited only by the reactive sites available for a given polymer, there is generally no practical purpose for excessively tagging a polymer. It is preferred to employ a polymer having more reactive sites (pendant groups of the Formula I) than required for exhaustion of the fluorescent derivatizing agent used. Hence while a 1 to 1 mole ratio of polymer reactive sites to fluorescent derivatizing agent is possible, and in fact less polymer reactive sites could reasonably be employed, it is desirable to have an excess of polymer reactive sites, and a soluble polymer of any significant molecule weight will have such an excess generally.

In the preferred embodiment, the starting material polymers of the present invention are water soluble polymers having molecular weights of from about 2,000 to about 100,000 and more preferably to about 50,000. In a further preferred embodiment, the starting material polymers of the present invention are water soluble polymers having at least 10 mole percent, and more preferably at least 30 or 50 mole percent, and more preferably at least 30 or 50 mole percent, of mer units of Formula II. In a more preferred embodiment, such polymers have at least 70 mole percent of mer units of the Formula II. Nonetheless (trans)amidation is believed to proceed with as little as about 1 weight percent of such mer units, particularly if excess derivatizing agent is used.

The fluorescent group(s) of the organic derivatizing agents may be polynuclear aromatic ring system, as mentioned above, must contain an amine moiety, and preferably a primary amine. There are a number and variety of such organic fluorescent amine-containing compositions that are commercially available. Many are commercially available as water soluble compositions, and others may become water soluble, or more water soluble, upon formation of the salts thereof. The fluorescent derivatizing agents useful for the present invention are available with distinguishable fluorescent spectral characteristics, and hence the polymers may be tagged with different fluorescent groups to, for instance, distinguish between different polymers by virtue of their resultant spectral characteristics.

The amine group of the organic fluorescent derivatizing agent may be covalently bonded directly to the polynuclear aromatic ring system, or it may be bonded to the ring system through an alkyl group. In other words, the group bonded to the ring system may be an amine, an amine substituted alkyl group, or an amine substituted alkyl group containing further substitution. A preferred amine-containing fluorescent derivatizing agent is one containing an alkyl amine; also one containing a primary amine covalently bonded to the ring system, preferred because such agents are generally readily available at very low cost.

A very useful group of organic fluorescent derivatizing agents contain a naphthalene ring system, which ring system is substituted with at least one primary amine and at least one sulfonic acid group. There are many compositions within this group that are commercially available at reasonable cost, and there are many compositions within this group, distinguished from one another by the number of amine and sulfonic acid substituents and, for a given number of each substituent, by the position of each substituent on the naphthalene ring system.

More specifically, amine-containing naphthalene compositions constitute a preference, including amino naphthalene monosulfonic acids, amino naphthalene disulfonic acids, amino naphthalene trisulfonic acids, and their sodium and/or potassium salt(s).

In preferred embodiments, the product polymer has different spectral properties than the organic fluorescent derivatizing agent, and hence the presence of product polymer tagged by the (trans)amidation reaction can be determined merely by the presence of its particular major fluorescent peak(s).

The polymers to be employed may vary as to the amount of pendant groups of Formula I, and some may have diverse pendant groups outside of Formula I. There may be derivatizations using a single type of pendant group within Formula I, that is, an acrylic acid homopolymer, and a number of polymers containing both (meth)acrylic acid and acrylamide units.

The polymers employed as starting material polymers for derivatization each preferably have more than 70 mole percent of mer unit within Formula II and weight average molecular weights of less than 50,000. The following abbreviations are used for the polymer units:

| AA | Acrylic acid |
| AcAm | Acrylamide |
| AMS | Sulfomethylacrylamide |
| VA | Vinyl acetate |
| MAA | Methacrylic acid |
| ACN | Acrylonitrile |

The combinations preferably include: AA/AcAm, AA/AcAm/AMS, AA/Ac/Am/MAA and AA/AcAm/ACN.

What is claimed is:

1. Method of determining the concentration of a water soluble carbonyl polymeric treating agent added to a circulating body of water confined in a water recirculating system, said treating agent being one which enhances the efficiency of equipment in the system by inhibiting scaling or corrosion or settling of particulates, comprising the steps of:
    dosing the body of water with a predetermined concentration of the treating agent bearing an amine-containing fluorescent moiety tag covalently bonded thereto;
    removing a sample of the body of water containing the tagged treating agent;
    analyzing the emissivity as a measure of the concentration of the treating agent in the sample, and
    adjusting the concentration of the treating agent accordingly as the analyzed sample exhibits a concentration departure from said predetermined concentration.

2. Method according to claim 1 wherein the treating agent is a polymer with a backbone containing acrylic acid tagged with an organic fluorescent derivatizing agent which is an organic fluorescent molecule that contains an amine group,

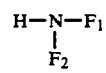

wherein one of $F_1$ is hydrogen or an organic fluorescent group and $F_2$ is an organic fluorescent group.

3. Method according to claim 2 wherein the organic fluorescent derivatizing agent is an amino naphthalene sulfonic acid or a salt thereof.

4. Method according to claim 3 in which the circulating body of water is contained within a cooling tower equipped for both blowdown and makeup.

5. Method according to claim 2 in which the circulating body of water is contained within a cooling tower equipped for both blowdown and makeup.

6. Method according to claim 2 wherein the treating agent is fed at a predetermined rate by a pump and including the steps of transforming emissivity to an analog signal; and transmitting the analog signal to a controller which adjusts the rate of the pump in accordance with the analog signal.

7. Method according to claim 1 in which the circulating body of water is contained within a cooling water equipped for both blowdown and makeup.

8. Method of determining the consumption of a water soluble carbonyl polymeric treating agent added to a circulating body of water confined in a water recirculating system, said treating agent being one which enhances the efficiency of equipment in the system by inhibiting scaling or corrosion or settling of particulates, comprising the steps of:

adding to the body of water both a predetermined concentration of said treating agent bearing an amine-containing fluorescent moiety tag covalently bonded thereto and, separately, an inert fluorescent tracer, inactive in the system, in a concentration equivalent to the concentration of the treating agent;

removing a sample of the body of water containing the fluorescent tracer and the tagged treating agent addition;

separately analyzing the emissivity of the treating agent and tracer in said body of water as a measure of their respective concentrations in the sample;

determining any difference between the analyzed concentration of the treating agent and that of the tracer as a departure from said equivalent concentration, and adjusting the concentration of said treating agent in said body of water based on said departure from said equivalent concentration.

9. Method according to claim 8 wherein the treating agent is a polymer with a backbone containing acrylic acid tagged with an organic fluorescent derivatizing agent which is an organic fluorescent molecule that contains an amine group, represented by

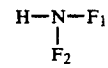

wherein $F_1$ is hydrogen and $F_2$ is an organic fluorescent group, and said derivatizing agent is an amino naphthalene sulfonic acid or a salt thereof.

10. Method according to claim 9 in which the circulating body of water is contained within a cooling tower equipped for both blowdown and makeup.

11. Method according to claim 8 in which the circulating body of water is contained within a cooling tower equipped for both blowdown and makeup.

* * * * *